(12) United States Patent
Sander

(10) Patent No.: US 8,508,230 B2
(45) Date of Patent: Aug. 13, 2013

(54) MICROSCOPE APPARATUS AND MICROSCOPY METHOD

(75) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 353 days.

(21) Appl. No.: 13/084,096

(22) Filed: Apr. 11, 2011

(65) Prior Publication Data

US 2011/0248713 A1 Oct. 13, 2011

(30) Foreign Application Priority Data

Apr. 9, 2010 (DE) .......................... 10 2010 003 836

(51) Int. Cl.
*G01V 3/00* (2006.01)
(52) U.S. Cl.
USPC .......................................... 324/318; 324/322
(58) Field of Classification Search
USPC ..................... 324/300–322; 600/407–445
See application file for complete search history.

(56) References Cited

U.S. PATENT DOCUMENTS

| | | | | |
|---|---|---|---|---|
| 5,736,958 | A | * | 4/1998 | Turpin ........................... 342/179 |
| 6,459,919 | B1 | * | 10/2002 | Lys et al. ....................... 600/407 |
| 6,765,718 | B1 | | 7/2004 | Spink et al. |
| 7,606,613 | B2 | * | 10/2009 | Simon et al. ................... 600/426 |
| 2011/0040171 | A1 | * | 2/2011 | Foley et al. .................... 600/411 |

FOREIGN PATENT DOCUMENTS

| | | |
|---|---|---|
| DE | 4032207 A1 | 4/1991 |
| DE | 10249025 B4 | 6/2007 |
| DE | 102007009543 A1 | 8/2008 |
| EP | 1224499 B1 | 8/2003 |
| EP | 1193520 B1 | 1/2006 |
| EP | 1152275 B1 | 6/2006 |
| EP | 1944617 A1 | 7/2008 |

* cited by examiner

*Primary Examiner* — Brij Shrivastav
(74) *Attorney, Agent, or Firm* — Patentbar International P.C.

(57) ABSTRACT

The present invention relates to a microscope apparatus (100) comprising
an operating microscope (20),
a magnetic resonance or MR apparatus (30),
a stand (10) that carries the operating microscope (20) and the MR apparatus (30),
at least one detector (14) for determining the spatial position of the MR apparatus (30) relative to the operating microscope (20),
a reflecting device (23) for reflecting an image obtained using the MR apparatus (30) into at least one observation beam path of the operating microscope (20),
a computer unit (40) which is connected to the at least one detector (14) and is arranged so as to determine the spatial position of the MR apparatus (20) relative to the operating microscope (30),
the computer unit (40) being connected to the reflecting device (23) and to the MR apparatus (30) and being arranged so as to provide the image that is to be reflected in for the reflecting device (23) on the basis of the spatial position determined for the MR apparatus (30) relative to the operating microscope (20).

10 Claims, 1 Drawing Sheet

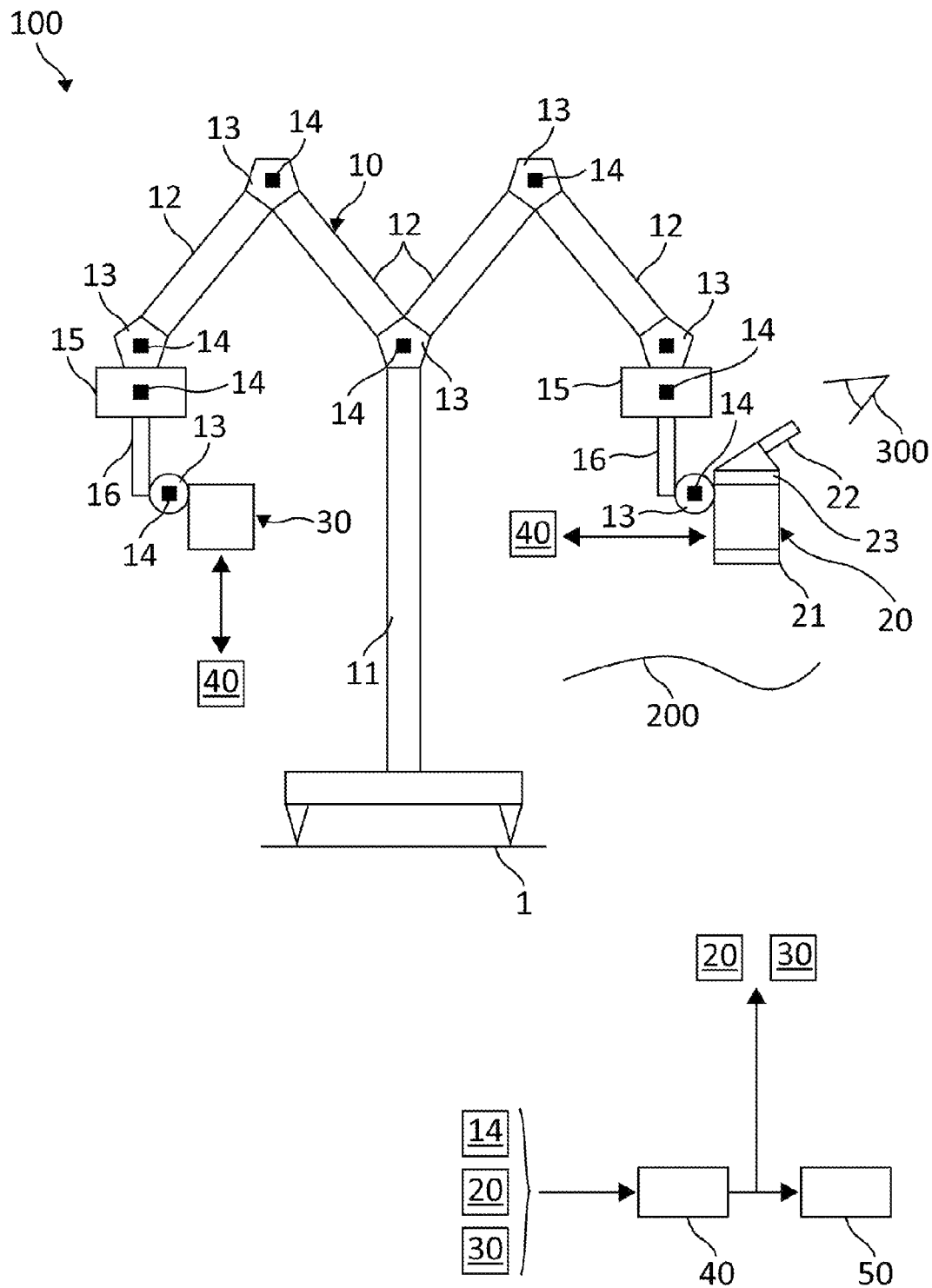

MICROSCOPE APPARATUS AND MICROSCOPY METHOD

CROSS-REFERENCE TO RELATED APPLICATIONS

This Application claims priority to German Patent Application No. DE 10 2010 003 836.9 filed on Apr. 9, 2010, that is incorporated herein by reference in its entirety.

FIELD OF THE INVENTION

The present invention relates to a microscope apparatus comprising at least one operating microscope and a magnetic resonance or MR apparatus and a method of microscopy using a microscope apparatus of this kind.

BACKGROUND OF THE INVENTION

Magnetic resonance methods are referred to by various abbreviations, for example MRT, MRI, NMR, etc. It is known to use MR methods for imaging in microscope-assisted surgery. For example, they can make it possible to distinguish more easily between healthy and diseased tissue, so that a surgeon can tell, for example, whether he has removed all the tumour tissue. Methods of this kind are therefore particularly suitable in fields such as brain surgery, for example, in which it is important to remove neither too much nor too little tissue.

Medical MR apparatus are very large pieces of equipment that generate strong magnetic fields. These magnetic fields and hence the imaging are disturbed by the iron-containing components that are present in conventional operating microscopes, which is why the MR equipment and operating microscope are often located in different rooms. MR-assisted operations of this kind are, however, very laborious as the patient often has to be transported back and forth during the operation while at the same time the alignment of the patient in the different apparatus has to be altered constantly. Therefore, the apparatus has to be realigned when any change is made.

To solve this problem it is proposed in EP 1 152 275 B1 to use an iron-free operating microscope on an iron-free stand in the same room as the MR apparatus. The drive used is an air motor which does not generate a magnetic field. Consequently, photographic images also can be produced intra-operatively during a break in the procedure without having to move the patient excessively.

One possibility for the advantageous use of CT section images is disclosed in DE 10 2007 009 543 A1. A microscope apparatus is described having a stand supporting a microscope and having at least one detector for determining the spatial position of the microscope. The microscope comprises a reflecting device for reflecting image data obtained pre-operatively, e.g. computer tomography section images, into the microscopic image. For example, a CT diagnosis section image can be reflected on to the particular site of the operation that is shown by the microscope image and thus be superimposed on the microscope image to enable the diagnosis and operation to be better matched to one other. The alignment of images obtained pre- or intra-operatively on the present microscope image, however, is very laborious.

There is a desire for an improved microscope apparatus and methods of microscopy which make it easier, in particular, to superimpose an MR image on the microscope image.

SUMMARY OF THE INVENTION

According to the invention a microscope apparatus and a method of microscopy having the features of the independent claims are proposed. Advantageous embodiments are the subject of the sub-claims and the description that follows.

The invention is based on the step of connecting an operating microscope to an MR apparatus such that the mutual alignment can easily be determined at any time. For this purpose, the operating microscope and MR apparatus are mounted on the same stand which is equipped with detectors for determining position. A computer unit is provided which ascertains the position of the stand and hence the position of the operating microscope and MR apparatus. This makes it possible to superimpose an image obtained using the MR apparatus accurately on the microscope image. There is no need to transport the patient. Nor is there any need to reposition or move the patient. Three-dimensional position detection of the microscope, as described in DE 10 2007 009 543 A1 mentioned hereinbefore, is not required, as only the relative arrangement of the microscope and MR apparatus is relevant.

The invention confers particular advantages particularly with respect to surgical interventions. The superimposing can be done quickly and easily, thus making it possible to increase the number of images that can be obtained during an operation. The length of time for which the operation may possibly have to be interrupted can be reduced significantly. Depending on the MR apparatus used, simultaneous image capture can also be carried out during the operation.

The superimposition may be carried out in particular using a reflecting apparatus as described in EP 1 224 499 B1. The stereomicroscope described therein can advantageously be used as an operating microscope.

The invention enables the operating surgeon always to adapt the visual conditions to the requirements in the optimum manner. For example, he can look only at the microscope image, only at an MR image or he can superimpose the images.

If the detectors are configured as articulated or joint sensors to determine the position of joints, the relative position of the two apparatus to each other can be determined very easily, as the dimensions of the arms of the stand or of the stand itself are known or, at the very least, can easily be determined If a stereomicroscope is used as the operating microscope, three-dimensional reflection is expediently carried out using different images for each observation beam path. The different images are produced by the computer unit, in particular.

Moreover, according to a preferred embodiment of the invention, it is envisaged that both apparatus be controlled via the computer unit, so that both the settings of the microscope such as e.g. the magnification, lighting, shutter, etc., and the settings of the MR apparatus can be input by the same person, in particular.

A single-sided MR apparatus may be used to particular advantage, as it can easily be connected to a stand for an operating microscope. Single-sided MR spectroscopy is described for example in EP 1 944 617 A1 and in the specifications cited in the associated Search Report, to which reference is hereby made for further details. Because of the advantageous construction of a single-sided MR apparatus in this case there are no special conditions regarding prevailing magnetic fields, with the result that conventional stands and operating microscopes can also be used. Compared with specially made constructions they are usually more tried and tested, more sophisticated and cheaper too. Overall, the microscope and MR apparatus form a unit, namely the microscope apparatus, which has significant advantages in the operating theatre. Instead of the patient being brought to the MR apparatus, the MR apparatus is brought to the patient.

The costs and space requirements of previous diagnosis machines can be reduced. Patient safety is increased.

MR diagnosis can take place directly during the operation as it can be carried out and controlled with the microscope apparatus. The diagnosis can advantageously also be made during the operation. The MR images - expediently suitably prepared —are reflected into the operating microscope and also controlled by the surgeon using the microscope control unit.

Advantageous applications for the invention can be found for example in ophthalmology for checking the positioning of an implanted lens (IOL), for examining the retina and/or the vitreous body. Another preferred field of use is the demarcation of tumours and distinguishing between tissues in brain and skin surgery. For example, one-, two- or three-dimensional profiles can be produced and spectral examinations can be carried out, avoiding the need for biopsies and examination of the biopsied tissue under an optical microscope.

Further advantages and embodiments of the invention will become apparent from the description and the attached drawings.

It will be understood that the features mentioned above and those yet to be explained hereinafter may be used not only in the particular combination specified but also in other combinations or on their own, without departing from the scope of the present invention.

The invention is schematically illustrated by means of an embodiment by way of example shown in the drawings and is described in detail hereinafter with reference to the drawings.

BRIEF DESCRIPTION OF THE DRAWINGS

FIG. 1 shows a microscope apparatus according to the invention in a schematic side elevation.

DETAILED DESCRIPTION OF THE PREFERRED EMBODIMENTS

FIG. 1 shows the schematic side elevation of a microscope apparatus 100 with an operating microscope 20 and an MR apparatus 30, which are supported on a stand 10. The operating microscope 20 and expediently also the MR apparatus 30 are mounted on the stand so as to be movable in all three directions in space (by translatory and rotary movement). The MR apparatus 30 is configured here as a single-sided MR apparatus and can be used for imaging, so as to produce, for example, magnetic resonance tomography sections (MRT). The data captured using the MR apparatus are transmitted to a computer unit 40 to generate MRT images.

In the embodiment in FIG. 1 there is a floor stand 10 that stands on a floor 1. As an illustration, the operating microscope 20 and the MR apparatus 30 are shown on either side of a stand column 11. However, it will be understood that both apparatus are freely movable relative to the column and are usually arranged close together during an operation so that using the two apparatus it is possible to obtain an at least overlapping part of an image. As the mountings of the operating microscope 20 and of the MR apparatus 30 are shown to be substantially identical here, only the mounting of the operating microscope 20 will be described in detail hereinafter.

The stand 10 comprises, in addition to the column 11 aligned perpendicularly to the floor 1, a number of arms 12 which are connected to one another by joints 13. The joints 13 may be in the form of hinges, ball and socket joints, etc. The joints 13 are each fitted with a detector 14 for determining the position of the joint, for example a joint sensor. The stand 10 advantageously has brakes which when activated fix the selected position. When they are deactivated, the respective joints 13 are freely movable.

Mounted on the outer arm 12 of the stand, via another joint 13, is a support arm 16 on which the microscope 20 is mounted. Between the support arm 16 and the stand arm 12 there may be an XY adjusting device 15 with sensor 14 by means of which the support arm 16 and the microscope 20 located thereon can additionally be motor-driven in a plane perpendicular to the plane of the drawing. The microscope 20 is movable by translatory motion in all three directions in space. It is also secured to the support arm 16 so as to be movable by rotary motion about all three directions in space.

The microscope 20 attached to the support arm 16 comprises—in known manner—a main objective 21 and a tube 22 with an eyepiece, these known components being shown in highly schematic form only.

Reference numeral 300 denotes the eye of the observer, shown schematically, for example the eye of a surgeon looking through the eyepiece of the microscope 20. The microscope 20 provides a magnified image of the object 200 (patient). The microscope may be fitted with a camera (not shown) which transmits the microscope image to the computer unit 40, for example for further processing, display and/or storage.

A reflecting device 23 is provided in the microscope 20 in front of the tube 22 with the eyepiece. Using a reflecting device 23 of this kind, image data, particularly the MRT images obtained using the MR apparatus 30, but also numerical data, graticules and the like, can be reflected into the microscope image and correlated with the particular microscope image. For example, an MRT diagnosis section can be reflected in at the particular site of the operation being shown by the microscope image and thus be superimposed on the microscope image to allow diagnosis and operation to be better matched to each other. Other items can also be reflected in using this method (numerical data, for example size ranges, graticules, indicator arrows, etc.).

The data from the sensors 14 are supplied to the computer unit 40, where they are processed. Connected downstream of the computer unit 40 there may be a monitor or an external computer unit 50 for optical display or further data processing. It is possible, in particular, to display on this monitor 50 the view that is seen by the observer or operating surgeon 300, i.e. particularly the microscope image with some data reflected into it. The monitor and/or external computer unit 50 are particularly suitable for remote monitoring or remote viewing of the investigation or operating procedure.

For reflecting data in, the computer unit 40 controls the reflecting device 23 in the microscope 20. Depending on the object range investigated, data obtained pre-operatively or intra-operatively with or without interrupting the intervention (i.e. simultaneously) (particularly the MRT images obtained using the MR apparatus 50, or numerical data) can be selected to suit the microscope image and superimposed thereon. The reflecting in of data is known per se, which means that reference can be made here to known literature such as e.g. EP 1 224 499 B1. The MR apparatus 30 is freely movable relative to the microscope 20, but their spatial positions relative to each another can be determined by evaluating the measured values supplied by the sensors 14 using the computer unit 40. Thus the computer unit 40 is able to prepare the image that is to be reflected in so as to obtain error-free superimposition. Three-dimensional reflection, for example using different images for each beam path of a stereo operating microscope, is also possible.

The invention claimed is:

1. A microscope apparatus (100) comprising
an operating microscope (20),
a magnetic resonance or MR apparatus (30),
a stand (10) that carries the operating microscope (20) and the MR apparatus (30),
at least one detector (14) for determining the spatial position of the MR apparatus (30) relative to the operating microscope (20),
a reflecting device (23) for reflecting an image obtained using the MR apparatus (30) into at least one observation beam path of the operating microscope (20),
a computer unit (40) which is connected to the at least one detector (14) and is arranged so as to determine the spatial position of the MR apparatus (20) relative to the operating microscope (30),
the computer unit (40) being connected to the reflecting device (23) and to the MR apparatus (30) and being arranged so as to provide the image that is to be reflected in for the reflecting device (23) on the basis of the spatial position determined for the MR apparatus (30) relative to the operating microscope (20).

2. The microscope apparatus according to claim 1, wherein the MR apparatus (30) is configured as a single-sided MR apparatus.

3. The microscope apparatus according to claim 1, wherein the computer unit (40) is arranged so as to control functions of the operating microscope (20) and/or the MR apparatus (30).

4. The microscope apparatus (100) according to claim 1, wherein a control unit is provided for a user to control the operating microscope (20) and/or the MR apparatus (30).

5. The microscope apparatus (100) according to claim 1, wherein the at least one detector is configured as a sensor (14) for detecting a joint position of the stand (10).

6. The microscope apparatus (100) according to claim 1, wherein the operating microscope (20) is configured as a stereomicroscope with at least two observation beam paths.

7. The microscope apparatus (100) according to claim 6, wherein the computer unit (40) is arranged so as to carry out a three-dimensional reflection using different images for each of the at least two observation beam paths.

8. The microscope apparatus (100) according to claim 1, wherein the computer unit (40) is arranged so as to control the reflecting device (23) so as to display only the microscope image, only the image that is to be reflected in or the two images superimposed.

9. The method of microscopy using a microscope apparatus (100) according to claim 1, wherein the spatial position of the MR apparatus (20) relative to the operating microscope (30) is determined and on the basis of the spatial position of the MR apparatus (30) determined relative to the operating microscope (20) the image to be reflected in for the reflecting device (23) is provided.

10. The method of microscopy according to claim 9, wherein an image obtained pre-operatively or intra-operatively using the MR apparatus (30) with or without interrupting the intervention is reflected into the reflecting device (23).

* * * * *